United States Patent [19]
Richter et al.

[11] Patent Number: 5,945,439
[45] Date of Patent: Aug. 31, 1999

[54] METHOD FOR DESTROYING OR INHIBITING GROWTH OF UNWANTED CELLS OR TISSUES

[75] Inventors: Anna Richter; Julia G. Levy; David Dolphin, all of Vancouver, Canada

[73] Assignee: QLT PhotoTherapeutics, Inc., Vancouver, Canada

[21] Appl. No.: 08/887,087

[22] Filed: Jul. 2, 1997

Related U.S. Application Data

[63] Continuation of application No. 07/930,165, Aug. 17, 1992, abandoned.

[51] Int. Cl.$^6$ ..................................................... A61K 31/40
[52] U.S. Cl. ............................................................. 514/410
[58] Field of Search ............................................ 514/410

[56] References Cited

U.S. PATENT DOCUMENTS

| | | | |
|---|---|---|---|
| 4,866,168 | 9/1989 | Dougherty et al. | 540/145 |
| 5,095,030 | 3/1992 | Levy et al. | 514/410 |

FOREIGN PATENT DOCUMENTS

| | | |
|---|---|---|
| 276 121 | 7/1988 | European Pat. Off. . |
| 352 076 | 1/1990 | European Pat. Off. . |
| WO 90/03187 | 4/1990 | WIPO . |

OTHER PUBLICATIONS

Tuzhikova et al., "Radioprotective Effect of Thioporphyrin–1 Derivatives on γ–Irradiated Mice", *Radiobiologia*, 18:6 842–47 (English Abstract of orginal Russian article only) 1977.
Bases et al., "Attempts as Modification of the Radiation Response of Neoplasms by the Administration of Hematoporphyrin". *Cancer*, 11:1119–24 (1958).
Moan et al., "X–irradiation of Human Cells in Culture in the Presence of Haematoporphyrin", *Int. J. Radiat. Biol.*, 40:107–109 (1981).
David Kessel, Tumor Localization and Photosensitization by Derivatives of Hematoporphyrin. A Review: *IEEE J. Quantum Electron* (1987) QE 23(10): 1718–20.
Chapman et al., "Inactivation of Viruses in Red Cell Concentrates with the Photo Sensitizer Benzoporphyrin Derivative (BPD)" (1991) Transfusion 31(Suppl): 47S Abstract S172.
North et al., "Viral Inactivation in Blood and Red Cell Concentrates with Benzoporphyrin Derivatives", *Blood Cells* (1992) 18:129–140.
C.H. Jamieson, "Preferential Uptake of Benzoporphyrin Derivative by Leukaemic versus Normal Cells", *Leuk. Res. (England)* (1990) 14(3):209–210.
Berns et al., "Response of Psoriasis to Red Laser Light (630 nm) Following Systemic Injection of Hemotoporphyrin Derivative", *Laser Surg. Med.* (1984) 4(10):73–77.
Anderson–Engels et al., "Fluorescence Diagnosis and Photochemical Treatment of Diseased Tissue Using Lasers: Part II", (1990) *Anal. Chem.* 62(1):19A–27A.
Ho et al., "Activity and Physicochemical Properties of Photofrin", (1991) *Photochemistry and Photobiology*, 54(1):83–87.
Mack et al., "Evaluation of the Combined Effects of Hematoporphyrin and Radiation", (1957), *Cancer*, 29:529–39.
Cohen et al., "Modification of Radiosensitivity by Porphyrins II. Transplanted Phabdomyosarcoma in Mice", (1966) *Cancer Research* 26 Part 1:1769–1773.
Schwartz et al., "Modification of Radiosensitivity by Porphyrins: Studies of Tumors and Other System", (1976) *Diagnosis and Therapy of Porphyrins and Lead Intoxication* 229–31.
Kostron et al., "The Interaction of Hematophyrin derivative, light, and ionizing radiation in a rat glioma model", (1986) *Cancer* 5:964–70.
Kostron et al., "Photodynamic Therapy is Potentiated by CO$^{60}$ and Intratumoral Injection of Hematoporphyrin Derivative", (1988) *J. of Neuro–Onc.* 6:185–191.
O'Hara et al., "Potentiation of Radiation–Induced Cell Kill by Synthetic Metalloporphyrins", (1989) *Int. J. Radiation Oncology Biol. Phys.* 16:1049–1052.
Bellnier et al., "Haematoporphyrin Derivative Photosensitizatrion and Gamma–radiation Damage Interaction in Chinese hamster Ovary Fibroblasts", (1986) *Int. J. Rad. Biol.* 50:659–664.
Fiel et al., "Radiation Modifying Effects of Meso–Tetraphenyl Porphyrins", (1975) *Res. Comm. Chem. Path. and Pharm.* 10(1):65–76.

*Primary Examiner*—Richard L. Raymond
*Attorney, Agent, or Firm*—Morrison & Foerster LLP

[57] ABSTRACT

This invention is a process for the use of a combination of ionizing radiation in conjunction with certain benzoporphyrin derivative compounds (BPD), preferably the compound benzoporphyrin derivative-monoacid ring-A (BPD-MA), to mediate the destruction of diseased or unwanted cells or tissues. Specifically, the invention is a method in which the sensitizer compounds are administered either systemically or locally to the diseased or unwanted tissue and irradiated with ionizing radiation (such as might be produced by a $^{60}$Co or x-ray source). The treatment with benzoporphyrin derivative compounds appears to sensitize the target cells or tissues in that those cells do not readily recover from irradiation exposure. In addition, the process may be used to lower the effective amount of radiation applied to a particular tissue target.

19 Claims, 8 Drawing Sheets

METHOD FOR DESTROYING OR INHIBITING GROWTH OF UNWANTED CELLS OR TISSUES

This application is a continuation of prior application Ser. No. 07/930,165, filed Aug. 17, 1992, now abandoned.

FIELD OF THE INVENTION

This invention is a process for the use of a combination of ionizing radiation in conjunction with certain benzoporphyrin derivative compounds (BPD), preferably the compound benzoporphyrin derivative—monoacid ring-A (BPD-MA), to mediate the destruction of diseased or unwanted cells or tissues. Specifically, the invention is a method in which the sensitizer compounds are administered to the diseased or unwanted tissue and irradiated with ionizing radiation (such as might be produced by a $^{60}$Co or x-ray source). The treatment with benzoporphyrin derivative compounds appears to sensitize the target cells or tissues in that those cells do not readily recover from irradiation exposure. In addition, the process may be used to lower the effective amount of radiation applied to a particular tissue target.

BACKGROUND OF THE INVENTION

The use of various porphyrin compounds in combination with irradiation—be the radiation visible or ionizing—in the treatment of diseased tissues is known. These treatments are often tumor-selective in that many porphyrin compounds accumulate at higher concentrations in tumor tissue than in normal tissue.

Porphyrin derivatives have been used in the treatment of tumors using the process of photodynamic therapy (PDT). In general, the PDT procedure involves administration of a sensitizer compound, such as the porphyrin derivatives, to target tissue and the subsequent treatment using light to that tissue. The PDT procedures function selectively to eradicate diseased tissue in the immediate area of the light source by generating singlet oxygen and activated molecules which damage tissue in that immediate area. Selectivity is attained through the preferential retention of the photosensitizer in rapidly metabolizing tissue such as tumors (Kessel, David, "Tumor Localization and Photosensitization by Derivatives of Hematoporphyrin. A Review" IEEE J. QUANTUM ELECTRON., QE 23(10): 1718–20 (1987)), virally infected cells (J. Chapman et al, "Inactivation of Viruses in Red Cell Concentrates with the Photo Sensitizer Benzoporphyrin Derivative (BPD)", TRANSFUSION 31(suppl): 47S Abstract S172, (1991) and J. North et al., "Viral Inactivation in Blood and Red Cell Concentrates with Benzoporphyrin Derivative", Blood Cells, 18: 129–140 (1992)), leukaemic cells (C. H. Jamieson, "Preferential Uptake of Benzoporphyrin Derivative by Leukaemic versus Normal Cells", Leuk. Res. (England) 1990, 14 (3), pp 209–210), psoriatic plaque (M. W. Rerns et al, "Response of Psoriasis to Red Laser Light (630 nm) Following Systemic Injection of Hematoporphyrin Derivative", Lasers Surg Med. 1984, 4(1) pp73–77), and atherosclerotic plaque (S. Andersson-Engels et al, "Fluorescence Diagnosis and Photochemical Treatment of Diseased Tissue Using Lasers: Part II", Anal. Chem. 62(1), 19A–27A (1990). The activation of the photosensitizer by visible light occurs only at the site at which visible light is present. Obviously, the photo-sensitizer-mediated destruction of tissue occurs only at the desired treatment site. The inactivated photosensitizer is nontoxic and will eventually be cleared from the body.

In a typical PDT treatment, PHOTOFRIN® porfimer sodium, BPD, or BPD-MA is injected into a patient. See, for instance, Ho et al., "Activity and Physicochemical Properties of PHOTOFRIN®", Photochemistry and Photobiology, 54(1), pp83–87 (1991); U.S. Pat. No. 4,866,168, to Dougherty et al. An appropriate dose is, e.g., 0.25–2.5 mg/kg of body weight, depending upon the diseased tissue and the choice of photosensitizer. At an appropriate time after photosensitizer administration, the diseased tissue or site is illuminated with a light source at an appropriate wavelength (630 nm for PHOTOFRIN® and 690 nm for BPD) to activate the photosensitizer. The thus-activated drug induces the formation of singlet oxygen and free radicals which damage the surrounding tissue. Both the diseased tissue and the vasculature feeding it are affected and the unwanted tissue is either directly destroyed or starved of oxygen and nutrients due to the occlusion of blood vessels. After the completion of the PDT, the treated tissue becomes necrotic and will either debride naturally or be debrided by the clinician.

Hematoporphyrin and PHOTOFRIN® have absorption spectra in the neighborhood of 630 nm. The absorption spectra of much blood and tissue is also in the same general spectral region. Consequently, much of the energy impinging upon the treated tissue is absorbed in the tissue itself, thereby limiting, in a practical sense, the physical depth to which the PDT treatment using hematoporphyrin and PHOTOFRIN® may be used. BPD-MA has an absorption spectra with peaks in longer wavelength regions, e.g., 690 nm. These compounds are viewed as improvements to the PDT treatment method in that the tissues do not absorb so much of the light energy and therefore allow increased depth of light penetration.

Nevertheless, PDT treatment for bulky or deep tumors, or for widespread disease, is limited by the depth of light penetration to only a few centimeters. Use of the ionizing radiation required by the instant invention will allow treatment of diseased or unwanted tissue at a depth much greater than with the PDT procedures.

An additional benefit to the procedure of this invention is that the benzoporphyrin derivative compounds leave the body much more quickly than the hematoporphyrin and PHOTOFRIN® materials. BPD leaves the body within a few days; the hematoporphyrin and PHOTOFRIN® materials may remain for weeks, leaving the patient's skin prone to sunburn in the interim.

The substitution of gamma radiation or x-rays for light in PDT has been investigated, with mixed results. Sometimes the porphyrin appears to protect the cells from radiation, sometimes sensitize those cells, and sometimes the compounds do nothing at all.

Mack et al., Cancer (1957) 29: 529–39 shows improved radiation tolerance in patients injected with hematoporphyrin prior to radiation therapy, but no extension of life over radiation-treated alone patients.

Novosel'tseva et al., Radiobiologiia (1979) 19(2): 297–301, tested the radioprotective effects of synthetic porphyrins.

However, Cohen et al., Cancer Research (1966) 26 Part 1: 1769–1773, reports that hematoporphyrin increased the sensitivity of rhabdomyosarcoma in mice to X-radiation. Hematoporphyrin complexed with copper exhibited no such enhancement.

Schwartz et al., Diagnosis and Therapy of Porphyrins and Lead Intoxication (1976) pp 229–31, shows the use of copper hematoporphyrin as a radiation sensitizer in the treatment of Katsumi dog tumors and various human tumors.

Kostron et al., *Cancer*, 5: 964–970 and Kostron et al., *Jour. of Neuro-Onc.* (1988) 6: 185–191, both discuss the effects of hematoporphyrin derivatives on rat gloime models in combination with stimulation by light and cobalt 60 or by a combination of the two. The use of radiation prior to administration of the porphyritic materials was not disclosed.

O'Hara et al., *Int. J. Radiation Oncology Biol. Phys.* (1989) 16: 1049–1052, discussed the effect of a group of water soluble, meso-substituted metalloporphyrins in combination with ionizing radiation on various tumor tissues.

A contrary teaching is found in Bellnier et al., *Int. J. Rad. Biol.* (1986) 50: 659–664. That document shows evidence that the mechanism of gamma-radiation and HPD photosensitization did not interact and that HPD did not augment the effects of x-radiation.

Also, Fiel et al., *Res. Comm. Chem. Path. and Pharm.* (1975) 10(1): 65–76, found that metal chelates of a mesoporphyrin in a lymphoid cell line were partially effective when added after irradiation as compared to pre-irradiation.

SUMMARY OF THE INVENTION

This invention is a process for augmenting the sensitivity and safety of radiotherapy for diseased or unwanted tissue by reducing the amount of radiation required for treatment through the co-treatment of the tissue with BPD, preferably BPD-MA. The BPD is typically administered to the tissue prior to the radiation step, although in certain circumstances, the BPD may be applied to the tissue or cell during or subsequent to the irradiation step if the so to be present at the surface of the cell at a time shortly after the irradiation is completed.

DETAILED DESCRIPTION OF THE INVENTION

This invention is a process involving the administration of BPD, BPD-MA, or their equivalents to diseased or unwanted tissue and to irradiation of the tissue with ionizing radiation. The ionizing radiation may be administered in relatively low dose due to the sensitization of those tissues by the treatment with BPD or BPD-MA.

Benzoporphyrin Derivatives

Figure 1A:
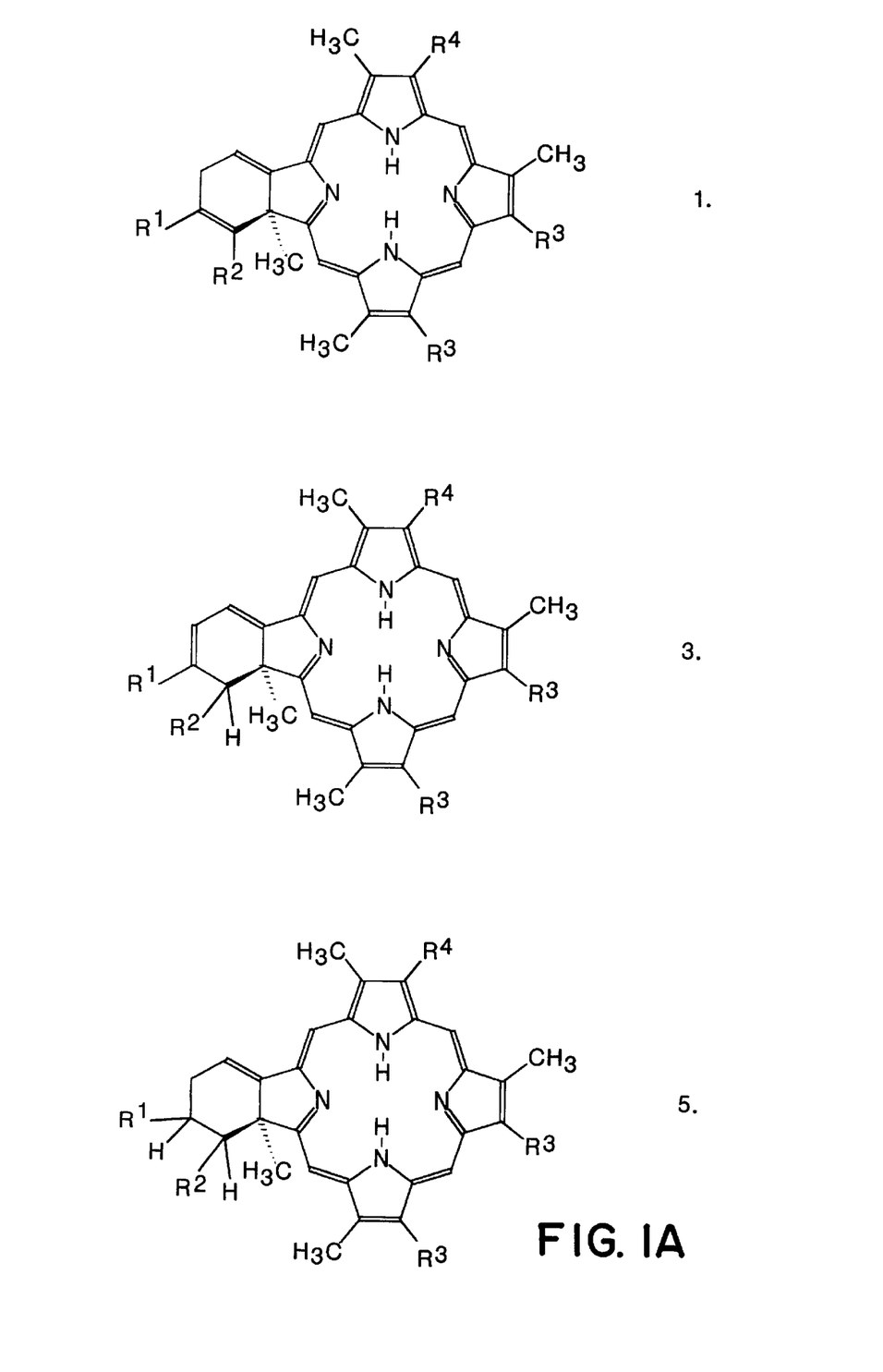
FIG. 1 shows the chemical structure of various porphyrins used in the treatment of diseased tissues.
Figure 1B:
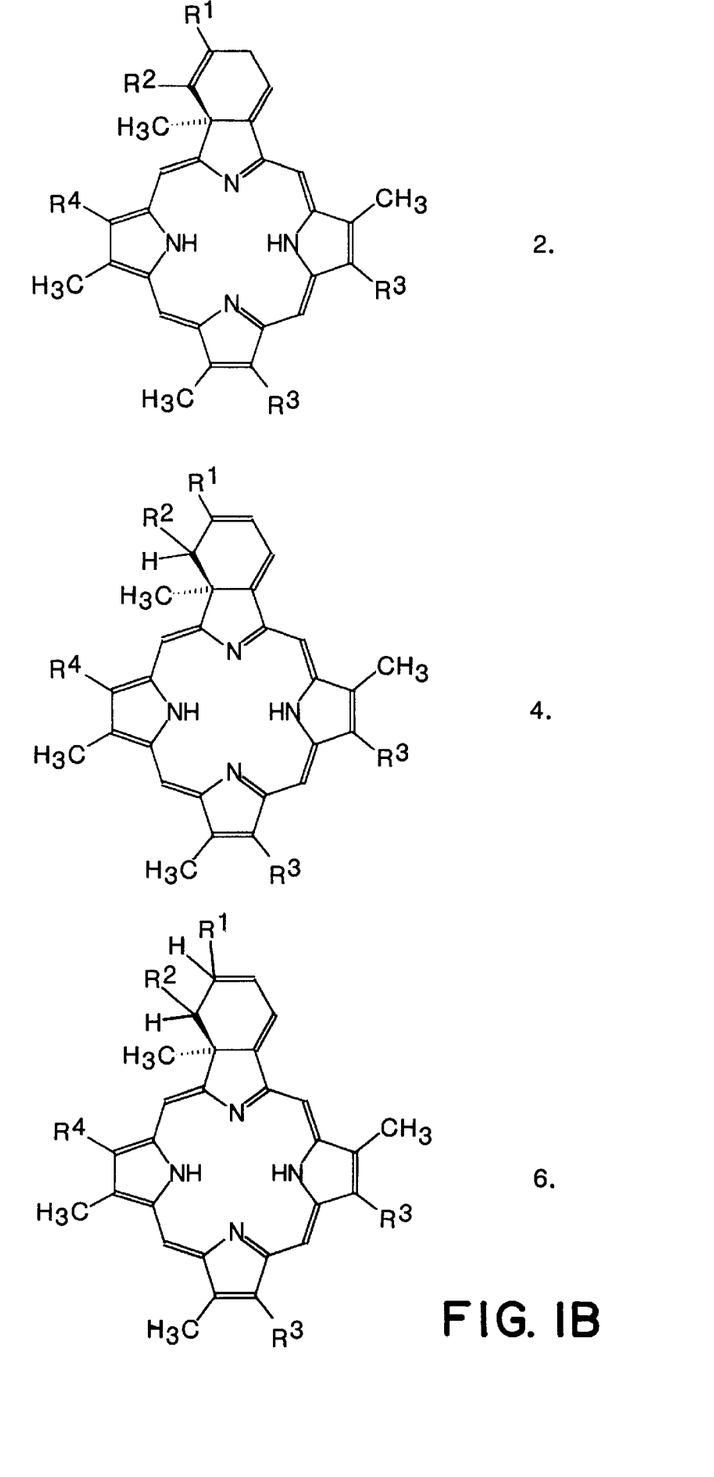
Figure 2:
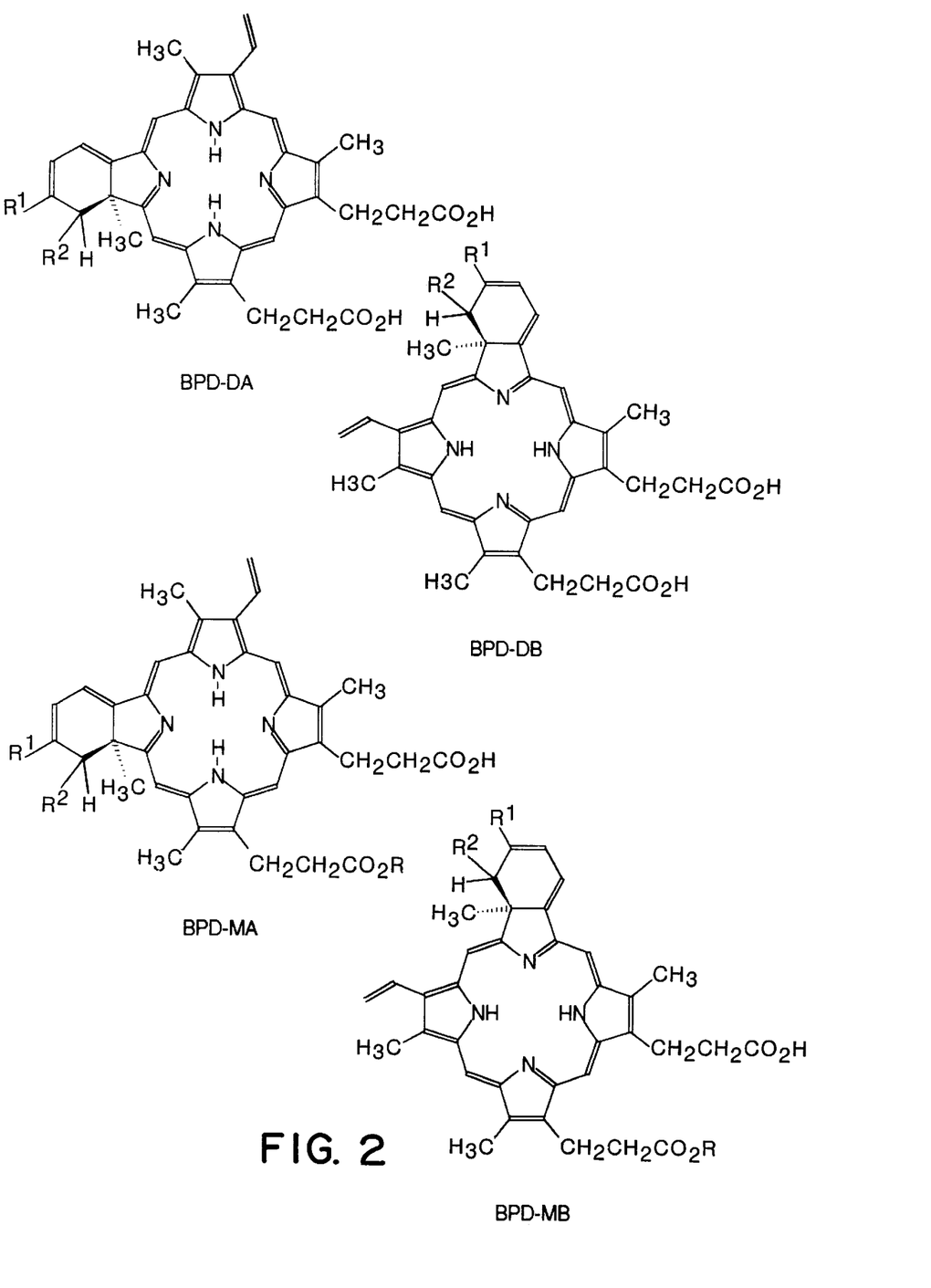
FIG. 2 shows the chemical structure of various BPD radiosensitizers used in the treatment of diseased tissues.

The radiosensitizers utilized in this invention are materials having the formulae specified in FIGS. 1 and 2, particularly those shown in FIG. 2, and most particularly BPD-MA. These compounds are well known and readily synthesized.

Specific preparations of the compounds useful in this invention or their precursors are in U.S. Pat. No. 4,920,143, to Levy et al. As described in that patent and the publications shown there, protoporphyrin-IX dimethylester, when reacted with strong Diels-Alder dienophile reagents such as tetracyanoethylene, is derivatized to hydrodibenzo derivative. However, when acetylene is derivatized with more weakly electron withdrawing groups and used as a Diels-Alder reagent, hydromonobenzo derivatives are formed. When the product is obtained directly from the reaction of protoporphyrin with, for instance, dimethylacetylene dicarboxylate (DMAD) the compounds found in Formulas 1 and 2 of FIG. 1 are generated. In FIG. 1, $R^1$ and $R^2$ represent the substituents on the original acetylene-derived Diels-Alder reagent, $R^1C\equiv CR^2$. $R^1$ and $R^2$ are, generally, lower alkyl, aryl, alkyl sulfonyl, or substituted aryl; preferably however they are carbalkoxy groups such as carbomethoxy or carboethoxy. $R^3$ represents substituents present on the porphyrin used in the reaction or substituents derived therefrom. In general, $R^1$ and $R^2$ are each, independently, moderately electron-withdrawing substituents, and are, most commonly, carbalkoxy, alkyl or aryl sulfonyl, or any other activating substituents which are not sufficiently electron-withdrawing to easily result in reaction with both A and B rings rather than reaction with only one. One of $R^1$ and $R^2$ may optionally be H while the other is an electron withdrawing substituent of sufficient strength to facilitate the Diels-Alder reaction.

As used herein, carboxy is —COOH and carbalkoxy is —COOR, wherein R is alkyl. Alkyl is a saturated hydrocarbon of 1–6 carbon atoms such as methyl, ethyl, isopropyl, n-hexyl, 2-methylpentyl, t-butyl, n-propyl, and so forth. Aryl or alkyl sulfonyl moieties have the formula $SO_2R$ wherein R is alkyl as above defined, or is aryl, wherein aryl is phenyl, e.g., phenylsulfonyl ($SO_2Ph$), optionally substituted with 1–3 substituents independently selected from halo (fluoro, chloro, bromo, or iodo), lower alkyl (1–4C) or lower alkoxy (1–4C). In addition, one or more $R^1$ or $R^2$ can itself be aryl, i.e., phenyl optionally substituted as above defined.

In addition, one or more of the esterified carboxy groups may be hydrolyzed.

As shown in FIG. 1, the adduct formed by the reaction of $R^1—C\equiv C—R^2$ with the protoporphyrin-IX ring system ($R^3$ is a protected form of 2-carboxyethyl such as 2-carbomethoxy ethyl or 2-carboethoxy ethyl; $R^4$ is $CHCH_2$) are compounds of the formulas 1 and 2 wherein the compound in formula 1 results from addition to the A ring and formula 2 results from addition to the B ring. In these resulting products of formulas 1 and 2, $R^4$ remains $CHCH_2$, however, this vinyl group is readily derivatized to other embodiments of $R^4$ by addition to or oxidation of the vinyl ring substituent of ring B in formulas 1 or ring A in Formulas 2. The addition products can be further substituted if the added substituents are functional nucleophiles—for example—Br may be substituted by —OH, —OR (R is alkyl 1–6 as above), or —$NH_2$, NHR, —$NR_2$, etc. In preferred embodiments, one of the added substituents is hydrogen and the other is selected from the group consisting of halo (fluoro, chloro, bromo or iodo), hydroxy, lower alkoxy, amino or an amide, sulfhydryl or an organo-sulfide or can be, itself, hydrogen. Thus, these compounds include various groups as $R^4$ as will be further described below.

$R^3$ in protoporphyrin-IX is 2-carboxyethyl (—CH$_2$CH$_2$COOH). However, the nature of $R^3$ (unless it contains a π-bond), is ordinarily not relevant to the progress of the Diels-Alder reaction. $R^3$ may be, for example, lower alkyl (1–4C), or ω-carboxyalkyl or carbalkoxy-alkyl (2–6C). The $R^3$ substituent may also be substituted with halogen as above-defined or with other nonreactive substituents. However, since the convenient starting materials for many of the compounds of the invention are the naturally occurring porphyrins, desirable substituents for $R^3$ are CH$_2$CH$_2$COOH or —CH$_2$CH$_2$COOR, wherein R is alkyl (1–6C).

It should be noted that while the nature of the $R^3$ substituent does not ordinarily influence the course of the Diels-Alder reaction by altering the nature of the diene substrate, derivatization may be necessary to promote the reaction by providing suitable solubility characteristics or to prevent interference with the reaction.

In certain subject compounds, it has been found advantageous to hydrolyze or partially hydrolyze the esterified carboxy group in —CH$_2$CH$_2$COOR. The hydrolysis occurs at a much faster rate than that of the ester groups of $R^1$, $R^2$, and the solubility and biological characteristics of the resulting compounds are more desirable than those of the unhydrolyzed form. Hydrolysis results in the diacid or monoacid products.

The hydro-monobenzoporphyrins which directly result from the Diels-Alder reaction described in the cited references may also be isomerized compounds of formulas shown as 3 and 4 of FIG. 1 by treatment with suitable reagents such as triethylamine (TEA) in methylene chloride or 1,5-diazabicyclo [5.4.0] undec-5-ene(DBU). The stereochemistry of the product is determined by the choice of reagent.

The depictions of compounds 3 and 4 in FIG. 1 do not show the relative position of the exocyclic methyl group (ring A of formulas 1 and ring B of formula 4) with respect to the $R^2$ substituent. Rearrangement using TEA gives cis geometry for the angular methyl group and $R^2$, while treatment with DBU results in the trans product. The cis product is evidently kinetically controlled since treatment of the cis product with DBU results in a further rearrangement to the generally more stable trans stereochemistry. Thus, formulas 3 and 4 of FIG. 1 show the rearranged products generically, from either TEA or DBU catalyzed rearrangement in rings A and B respectively.

In addition, the Diels-Alder products can be selectively reduced such as by treating with hydrogen in the presence of palladium on charcoal to give the saturated ring analogs, shown as formulas 5 and 6 in FIG. 1, corresponding to the respective Diels-Alder products of rings A and B.

The description set forth above with respect to the compounds of formulas 1 and 2 concerning derivatization by conversion of the remaining vinyl substituent ($R^4$) and with respect to variability of —$R^3$ applies as well to the compounds of formulas 3, 4, 5, and 6.

The compounds of formulas 3 and 4, and especially those which have hydrolyzed or partially hydrolyzed carbalkoxy groups in $R^3$, may be prepared as the free acid or in the form of salts with organic or inorganic bases.

It will be noted that many of the compounds of FIG. 1 contain at least one chiral center and therefore exist as optical isomers. The conjugates and methods of the invention include compounds having both configurations of the chiral carbons, whether the compounds are supplied as isolates of a single stereoisomer or are mixtures of enantiomers and/or diasteriomers. Separation of mixtures of diasteriomers may be effected by any conventional means; mixtures of enantiomers may be separated by usual techniques of reacting them with optically active preparations and separating the resulting diasteriomers or by chromatography using chiral supports.

It should further noted that the reaction products may be unseparated mixtures of A and B ring additions, e.g., mixtures of formulas 1 and 2 or 3 and 4 or 5 and 6. Either the separated forms—i.e., formula 3 alone or 4 alone, or mixtures in any ratio may be employed in the methods of therapy and diagnosis set forth herein.

The name "dihydro"-monobenzoporphyrin describes the direct and rearrangement products of the Diels-Alder reaction of the porphyrin ring system with $R^{1-}C\equiv C-R^2$; "tetrahydro"-monobenzoporphyrin describes the foregoing reduced products of formulas 5 and 6, and "hexahydro"-monobenzoporphyrin describes the analogs containing the exocyclic "benzo" ring completely reduced. Hydro-monobenzoporphyrin is used generically to include all three classes of oxidation state.

Additionally, the invention is directed to use of the compounds shown in FIG. 1 wherein:

$R^1$ and $R^2$ are as above defined, each $R^3$ is independently —CH$_2$CH$_2$COOR$^{3'}$ wherein $R^{3'}$ is H or alkyl(1–6C).

$R^4$ is CHCH$_2$, CHOR$^{4'}$, COOR$^{4'}$, CH(OR$^{4'}$) CH$_3$, CH(OR$^{4'}$)CH$_2$OR$^{4'}$, —CH(SR$^{4'}$(SR$^{4'}$)CH$^3$, —CH (NR$^{4'}$)CH$_3$, —CH(CN)CH$_3$, —CH(COOR)$^{4'}$CH$_3$, —CH(OOCR$^{4'}$)CH$_3$, —CH(halo)CH$_3$, and —(CH (halo)CH$_2$(halo), wherein $R^{4'}$ is H, alkyl(1–6C), or an organic group of <12C derivatizable as shown, and wherein when $R^4$ is CHCH$_2$, both $R^3$ cannot be 2-carbalkoxy ethyl.

Compounds of the formulas 3 and 4 and mixtures thereof are suitable; as are those where $R^1$ and $R^2$ are the same and are carbalkoxy, especially carbomethoxy or carboethoxy; also suitable are those wherein $R^4$ is —CHCH$_2$, CH(OH) CH$_3$ or —CH(halo)CH$_3$.

The compounds of formulas shown in FIG. 1 include those wherein $R^4$ is formed by addition to the vinyl groups of initial protoporphyrin products. Thus, $R^4$ can be any substituent consistent with a facile addition reaction. Thus, both added substituents can be, for example, OH or halo, and these substituents can be further substituted.

The vinyl group can also be oxidized to obtain $R^4$ as CH$_2$OH, —CHO or COOH and its salts and esters.

Thus, in general, $R^4$ represents any substituent to which the vinyl group —CH=CH$_2$ is readily converted by oxidation or addition. Typical $R^4$ substituents include:

CH(OH)Me, —CHBrMe, —CH(OMe)Me, —CH(pyridinium bromide)Me, —CH(SH)Me and the disulfide thereof, —CHOHCH$_2$OH, and —CHO.

FIG. 2 shows four particularly preferred compounds of the invention. These compounds are collectively designated benzoporphyrin derivative (BPD) are forms of the compounds having formula 3 or 4 in FIG. 1. These materials are hydrolyzed or partially hydrolyzed forms of the rearranged products of formula 3 and 4, wherein one or both of the protected carboxyl groups of $R^3$ are hydrolyzed. The ester groups at $R^1$ and $R^2$ hydrolyze relatively so slowly that conversion to the forms shown in FIG. 2 is easily effected.

For purposes of this description, $R^3$ is —CH$_2$COOR$^{3'}$. As shown in FIG. 2, each $R^{3'}$ is H in preferred compound BPD-DA, $R^1$ and $R^2$ are carbalkoxy, and derivatization is at ring A; BPD-DB is the corresponding compound wherein derivatization is at ring B. BPD-MA represents the partially hydrolyzed form of BPD-MA, and BPD-MB is the corresponding compound wherein derivatization is at ring B. BPD-MA represents the partially hydrolyzed form of BPD-DA, and BPD-MB, the partially hydrolyzed form of BPD-DB. Thus, in these latter compounds, $R^1$ and $R^2$ are carbalkoxy, one $R^{3'}$ is H and the other $R^{3'}$ is alkyl(1–6C). The compounds of formulas BPD-MA, -MB, -DA and -DB may be employed in the methods of the invention.

In another aspect, the invention is directed to compounds of the formulas shown in FIG. 2 wherein $R^1$ and $R^2$ are carbalkoxy, especially carbomethoxy or carboethoxy.

As noted above, especially preferred are those variations of BPD-MA in which $R^1$ and $R^2$ are carbalkoxy, especially carbomethoxy or carboethoxy. In each instance one or the other of $R^1$ or $R^2$ may be H.

BPD-MA may also be conjugated to specific ligands reactive with a target, such as receptor-specific ligands or immunoglobulins, or immunospecific portions of immunoglobulins, permitting them to be more concentrated in a desired target tissue or substance. This conjugation may permit further lowering of the ionizing radiation dose level as discussed below. This invention relates to methods of locating or placing cytotoxicity at target tissues.

Additionally, BPD-MA may be formed into a conjugate such as IG-L-BPD-MA, where IG represents an immunoglobulin or an immunologically reactive portion thereof, and L represents either a covalent bond linking these components or a linking moiety covalently linked to each of the IG and BPD-MA. Of course, IG may be replaced in such conjugates by other carriers which will covalently bond to the BPD molecule, e.g., PVA and dextran.

Administration and Use

The method of radiosensitizing diseased tissue using BPD is useful where a reduced radiation dose and a safe and effective porphyrin radiosensitizer are desired. The compounds have no direct biological effect and are therefore nontoxic. The compounds are thought to operate by inhibiting repair of the damage to diseased tissue affected by radiation.

Typical indications for this treatment include destruction of tumor tissue in solid tumors, treatment of topical tumors or skin disease including papillomavirus infections; and treatment of biological fluids such as blood for leukemia or infection. The radiosensitizer may be employed alone, or may be formulated into pharmaceutical compositions for administration to the subject or applied to an in vitro target using techniques known generally in the art. A summary of such pharmaceutical compositions may be found, for instance, in *Remington's Pharmaceutical Sciences*. The process may be carried out in vitro by, e.g., removing a fluid, such as blood, from the body which may have been treated in vivo or in vitro with BPD, BPD-MA or the equivalents, and irradiated before returning it to the body.

BPD, BPD-MA, and their conjugates may be administered systemically or locally. They may be used alone or as components of mixtures.

Injection may be intravenous, subcutaneous, intramuscular, or even intraperitoneal. Injectables may be prepared in conventional forms, either as liquid solutions or suspensions, solid forms suitable for solutions or suspension in liquid prior to injection, or as emulsions. In particular, liposomal or lipophilic formulations are most desirable. If suspension or emulsion are utilized, suitable excipients include water, saline, dextrose, glycerol, and the like. These compositions may contain minor amounts of nontoxic, auxiliary substances such as wetting or emulsifying agents, pH buffering agents, and the like. Oral formulations may also be appropriate in those instances where the radiosensitizer may be readily administered to the diseased tissue via this route.

If the treatment is to be localized, such as for the treatment of superficial tumors or skin cancers, the BPD, BPD-MA, their equivalents, or conjugates may be topically administered using standard topical compositions including lotions, suspensions, or pastes. The quantity of radiosensitizer to be administered depends on the condition to be treated, the mode of administration, the individual subject, and the judgment of the practitioner. Depending on the specificity of the preparation, smaller or larger doses may be needed. For compositions which are highly specific to target tissue, such as those which comprise conjugates of the radiosensitizer with a highly specific monoclonal immunoglobulin preparation or specific receptor ligand, dosages in the range of 0.05–1 mg/kg are suggested. For compositions which are less specific to the target tissue, larger doses, up to 1–10 mg/kg, may be desirable. The foregoing ranges are merely suggestive in that the number of variables with regard to an individual treatment regime is large and considerable excursion from these recommended values may be expected.

The dosage of ionizing radiation desired in this process is preferably less than about 500 rads; more preferably between 10 and 200 rads. The ionizing radiation may be x-ray, but preferably is gamma radiation as from a $^{60}$Co source. The level required is lower than that needed in most irradiation processes.

Indeed, use of BPD, BPD-MA, their equivalents and conjugates (whether applied to the target cell before irradiation or very shortly thereafter) significantly lowers the dose of irradiation need to in isolation to destroy the unwanted cell or to inhibit its growth.

The examples which follow are intended to demonstrate the efficacy of the invention and to assist in the practice of the invention. They are intended only to be examples and not to limit the invention in any way.

EXAMPLES

Example 1

This comparative example shows the in vitro administration of PHOTOFRIN® to cancer cells and to normal bovine endothelial cells, followed by exposure to ionizing radiation.

In this example, the cells (a. P815 tumor cells—mastocytoma in DBA/2 mice; b. M1 tumor cells—3-methylcholanthrene-induced rhabdomyosarcoma in DBA/2 mice; c. 3905A cells—endothelial cells from bovine aorta) were incubated in 96-well plates with PHOTOFRIN® for 5 or 24 hours in culture medium containing 10% fetal calf serum (FCS). The range of concentrations tested was between 0.5 and 20 μg/ml. Immediately following the incubation, the cells were exposed to radiation from a $^{60}$Co source. Doses chosen were below $LD_{50}$. Cells incubated with various concentrations of PHOTOFRIN® and not irradiated were used to determine the baseline toxicity of the drugs. The survival of cell was measured at 48 to 96 hours after irradiation using a colorimetric method (MTT). The radiosensitizing effect of the drugs was determined by relating the survival of irradiated cells (cultured in the presence of the drug) to the survival of irradiated cells (cultured in the absence of the drug).

Figure 3A:
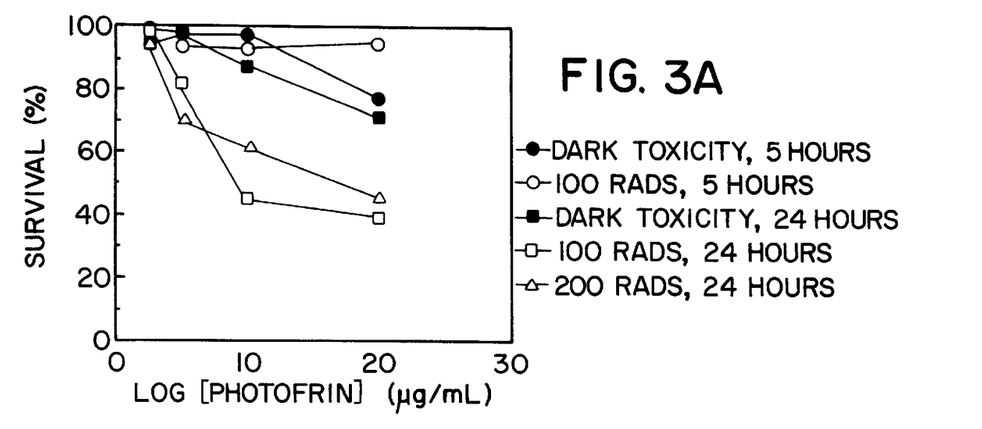
FIGS. 3A, 3B and 3C show the results of in vitro treatment of tumor cells ((P815 and M1) and normal cells (3905A)) with PHOTOFRIN® followed by the use of ionizing radiation.
Figure 3B:
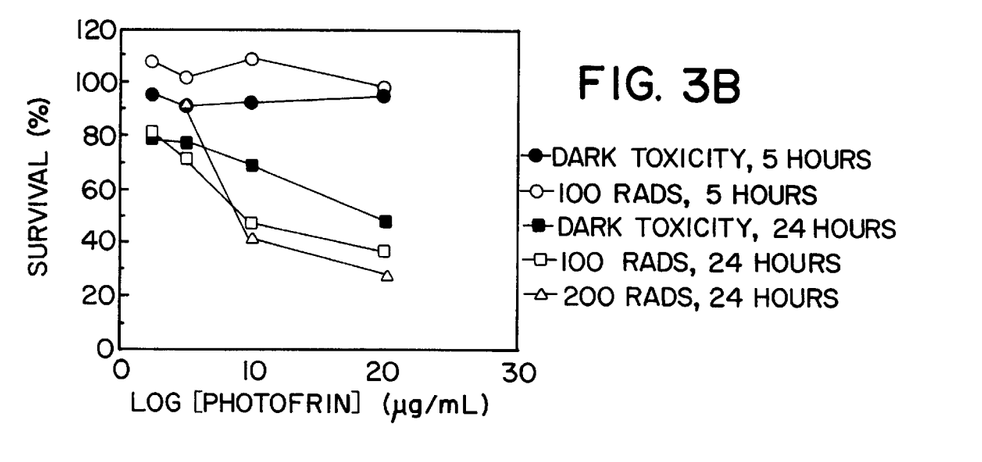
Figure 3C:
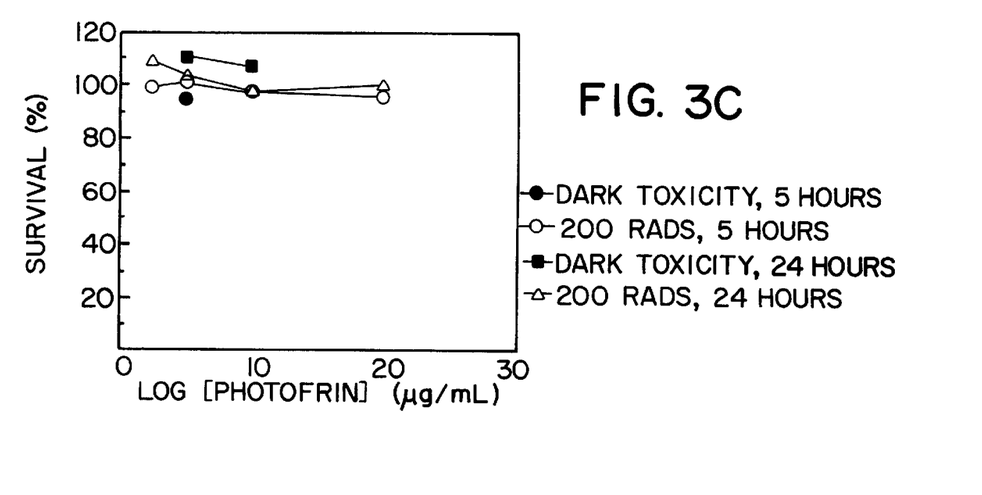

FIGS. 3A, 3B, and 3C show the results of these runs. PHOTOFRIN® clearly radiosensitizes tumor cells in vitro. Although the results show that PHOTOFRIN® alone has some tendency at higher concentrations to lower the survival of the PB15 tumor cells (at 20 μg/ml showed 80% survival), the subsequent radiation either by doses of either 100 or 200 rads from a $^{60}$Co source lowered the survivability by a significant factor. As shown in FIG. 3A, the open square (100 rads) and the open triangle (200 rads) showed survival percentages of only 40–50%.

Similarly, as is shown in FIG. 3B, the survival of M1 tumor cells at 96 hours was lower in those instances where the cells had been irradiated either at 100 or 200 rads than the same cells which had been incubated with PHOTOFRIN® in medium containing 10% FCS for 24 hours. The cells incubated with PHOTOFRIN® for only five hours survived, whether irradiated or not.

FIG. 3C shows that, in vitro, non-tumor cells such as 3905A bovine endothelial cells show high survival rates when treated with PHOTOFRIN® for various periods of time, whether then treated with the higher dose of radiation or not. After 96 hours, nearly all of the cells survived after treatment with 200 rads from a $^{60}$Co source.

Example 2

This example shows a parametric study on the in vitro sensitization of murine mastocytoma P815 for gamma radiation.

Figure 4A:
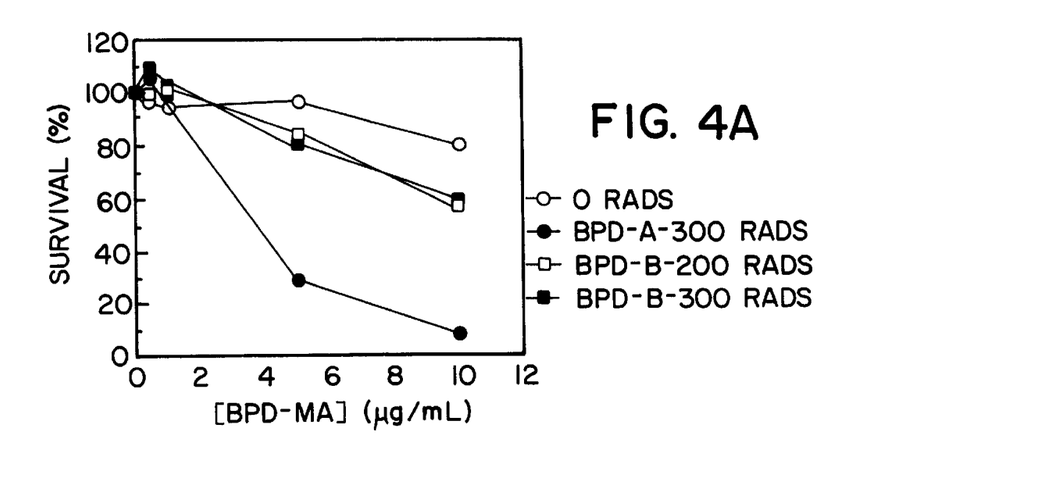
FIGS. 4A, 4B and 4C show the effect of several parametric variables on the in vitro survival of cancer cells (P815).

The P815 cells, either alone or with varying doses of BPD-MA, were incubated for 24 hours in DME+10% FCS. At 24 hours, the medium was changed and the cells were incubated for a further 24 hours, at which time growth was determined using an MTT assay as described in Example 1. Irradiated cells received 300 rads at time 0 and were treated in the same manner as the non-irradiated control cells. However, the irradiation time was chosen at 4 hours to allow for cellular uptake of the porphyrins. As is shown in FIG. 4A, the dosage of BPD-MA affects the survival rate of P815 cells as does the radiation dosage. In that Figure, the control received only BPD-MA and no radiation and survival was quite high (greater than 80%). When the cells pre-incubate with BPD were irradiated either at 200 or 300 rads, the survival rate declined somewhat linearly with increasing concentration. In contrast, the cells receiving BPD after irradiation with 300 rads (solid dots in FIG. 4A), the percent of survival was significantly lower still. This demonstrated that the time of addition, as well as the concentration of BPD, provided significantly different effects upon survival of the cells. It is clear that P815 cells exposed to BPD (at 10 μg/ml) and 300 rads are essentially eliminated but those cells exposed either to radiation alone or to the drug alone did not appear to suffer substantial damaging effects.

Figure 4B:
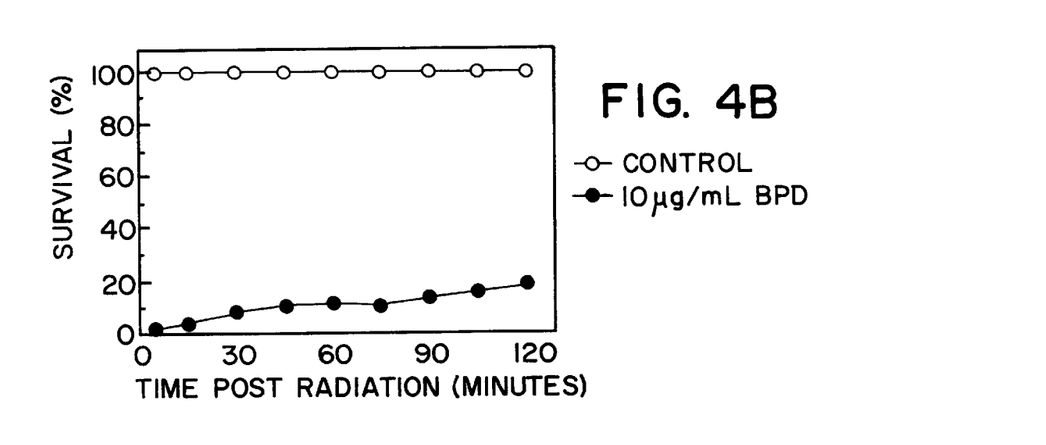

FIG. 4B shows the results of adding BPD-MA at various times after radiation. In this experiment, P815 tumor cells were radiated with $^{60}$Co at 300 rads. BPD-MA at 10 μg/ml was added to the P815 cells at intervals between 5 and 120 minutes after radiation. Significant enhanced killing was seen. The addition of the BPD-MA was most effective when added shortly after the time of radiation. This suggests that BPD-MA interferes in some way with cellular repair mechanisms following irradiation.

Figure 4C:
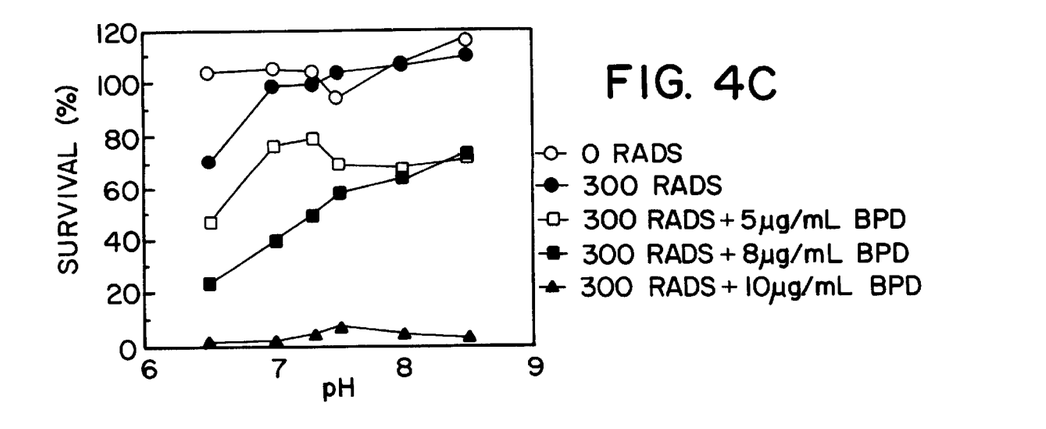

FIG. 4C shows the effect of pH on the sensitizing effect of BPD-MA. In this series of tests, P815 cells were treated in various ways. In each instance the cells were exposed to 300 rads of $^{60}$Co irradiation and then exposed for 24 hours of various doses of BPD-MA (at 5, 8 and 10 μg/ml) in media at pHs between 6.5 and 8.5. At 24 hours, the growth medium was replaced with regular culture medium and the cells were cultured for another 24 hours at which time the cell viability was determined by MTT essay. FIG. 4C demonstrates that for all cultures, all irradiated cells were somewhat negatively effected at pH's of 7 or below.

Example 3

In this example, the effects of related porphyrins, PHOTOFRIN® , hematoporphyrin IX, and BPD-MA were compared to show the specific efficacy of BPD-MA in relation to the other porphyrins.

Figure 5A:
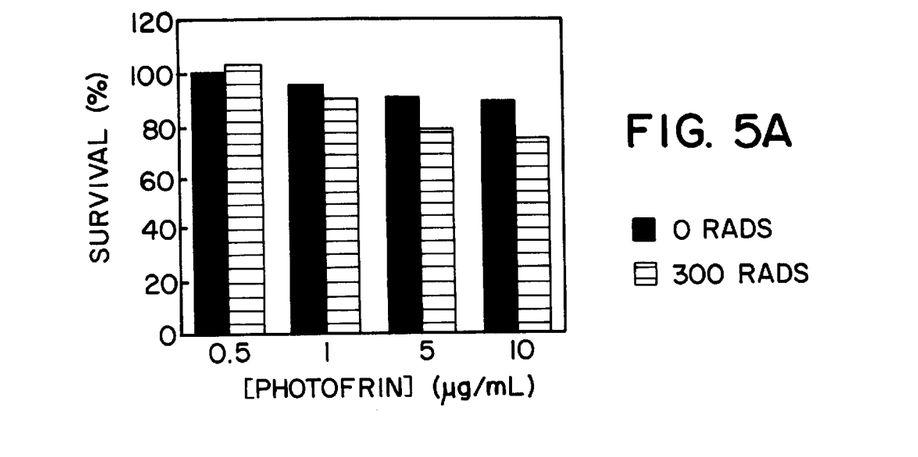
FIGS. 5A, 5B and 5C show the in vitro effect of radiation followed by application of PHOTOFRIN® hematoporphyrin or the inventive BPD-MA on survival of cancer cells (P815).

FIG. 5A shows the effect of the addition of PHOTOFRIN® at various concentrations from 0.5 to a 10 μg/ml to P815 cells which either were not irradiated or were irradiated with 300 rads of $^{60}$Co radiation. The PHOTOFRIN® S was added to the cells immediately after irradiation. As is shown in FIG. 5A, the difference between cell survival in the presence of PHOTOFRIN® with and without the subsequent irradiation is not significant. Consequently, the various diporphyrins found in PHOTOFRIN® can be judged not to have the same in vitro radiosensitizing effect as does BPD-MA.

Figure 5B:
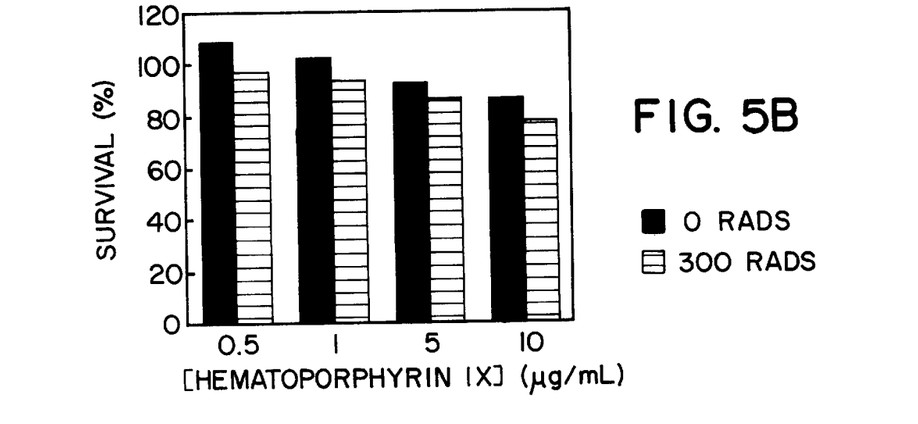

FIG. 5B shows a similar demonstration in which P815 tumor cells were irradiated with 300 rads of $^{60}$Co gamma radiation and immediately treated with various concentrations of hematoporphyrin IX. The concentrations were 0.5, 1, 5, and 10 μg/ml of the drug. Again, only marginal differences were seen between the irradiated cells which had been treated with the hematoporphyrin IX in comparison to the cells which had been only cultured with the hematoporphyrin IX.

Figure 5C:
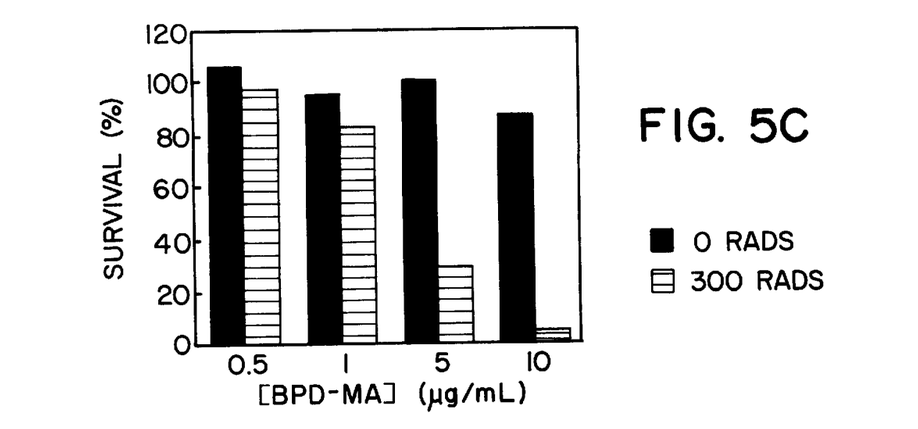

FIG. 5C shows the sensitizing effect of gamma radiation upon the subsequent treatment with BPD-MA. In this example, P815 tumor cells were irradiated at a level of 300 rads with $^{60}$Co gamma radiation. BPD-MA at various concentrations was then added to the test cells within 5 to 10 minutes after irradiation. The same concentration of BPD-MA was added to control non-irradiated cells. The survival of cells was measured at 24 hours after irradiation by means of MTT calorimetric assay. It is quite clear that the radiosensitizing efficacy of BPD-MA is significantly higher than that of either of the two porphyrin materials shown in FIGS. 5A and 5B. At a concentration of 5 µg/ml, the percent of survival was only 30% and at a concentration 10 µg/ml, the percent of survival for the P815 tumor cells was in the neighborhood of 2%.

Example 4

In view of the in vitro results shown in Examples 1 through 3, in vivo tests were believed appropriate.

In this example, groups of DBA/2 mice were injected intradermally with M1 cells (rhabdomyosarcoma cell line) when the tumor cells became palpable at about 5 mm², the animals were treated in various ways and the tumor size was monitored. The animals were randomized and treated in the following ways:

(a) No drug—no radiation.
(b) 10 µg of BPD-MA per kg of body weight administered intravenously.
(c) 400 rads of radiation to the body.
(d) BPD-MA (10 µg/kg of body weight administered intravenously before 400 rads of $^{60}$Co irradiation, and
(e) 400 rads of irradiation given prior to 10 µg BPD-MA per kg of body weight given intravenously.

The tumors were followed by measuring daily using a blinded procedure.

Figure 6A:
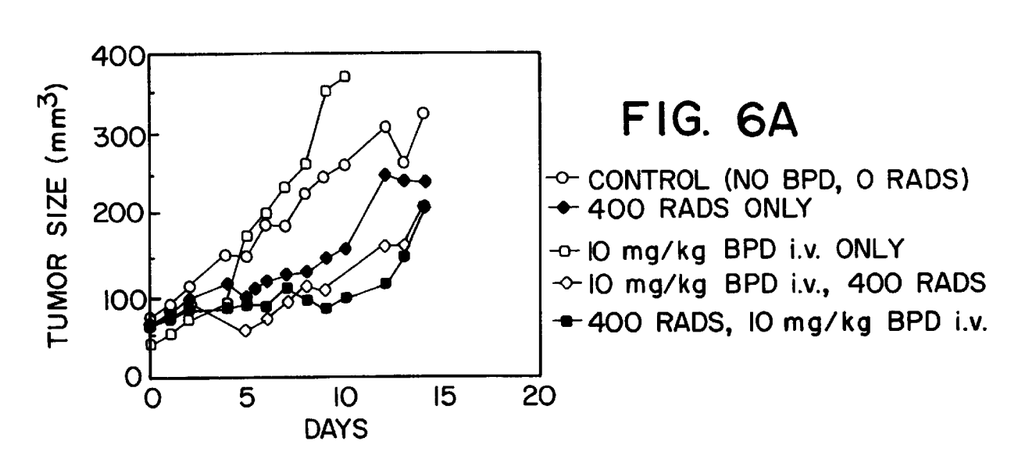
FIGS. 6A and 6B show the results of tests in vivo on the growth of tumors with various BPD-MA treatments.

FIG. 6A shows the relative size of the tumors as a function of time. FIG. 6A shows that radiation alone slowed the tumor growth in comparison to the tumors in mice which had neither drug nor radiation. The use of BPD-MA by itself, without radiation, appeared to accelerate the growth of the tumors in the five to ten day period. The administration of BPD either before or after irradiation appeared to significantly slow tumor growth.

Figure 6B:
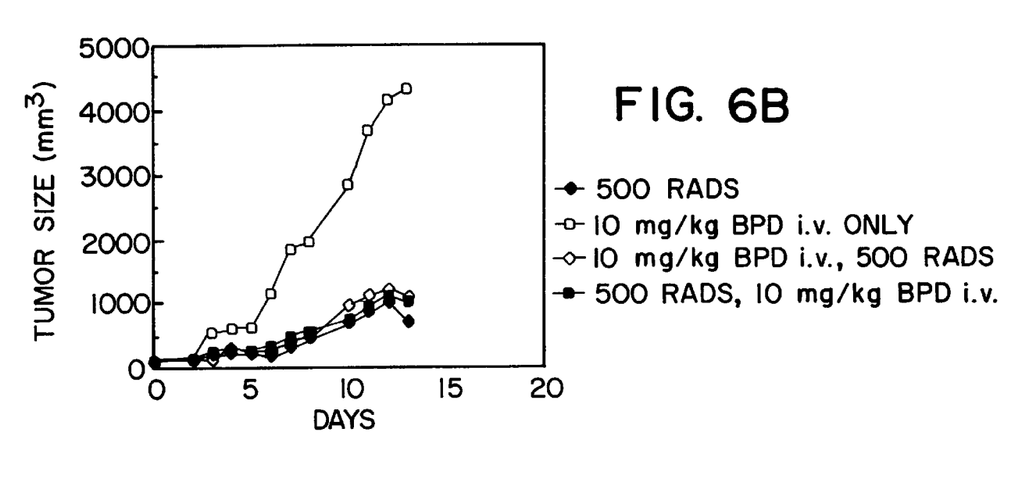

FIG. 6B shows a second experiment which differed from the experiment just above only regarding the radiation dose. The results shown in FIG. 6B were obtained using a radiation dose of 500 rads rather than 400 rads as was shown immediately above. As may be seen from the FIG. 6B, no substantial differences were observed amongst any of the tumors which had been irradiated with the 500 rads dosage. It is believed that this clustering of results resulted from the presence of irradiation doses sufficiently large that no additive effect was seen with the prior or post administration of BPD-MA.

Example 5

This example shows the effect of BPD-MA and radiation on the in vivo growth of P815 tumors in DBA/2 mice.

In this example, shaved mice were again injected with tumor cells. In this instance the animals were injected subcutaneously with 10⁴ P815 cells. When the tumors became palpable at about 5 mm, animals were treated in various ways and the tumor size was monitored. The animals were randomized into three groups, which groups were treated in the following manner:

(a) No drug, no radiation,
(b) Radiation with 200 rads,
(c) BPD-MA (10 mg of drug per kg of body weight) administered intravenously prior to 200 rads of irradiation.

Figure 7:
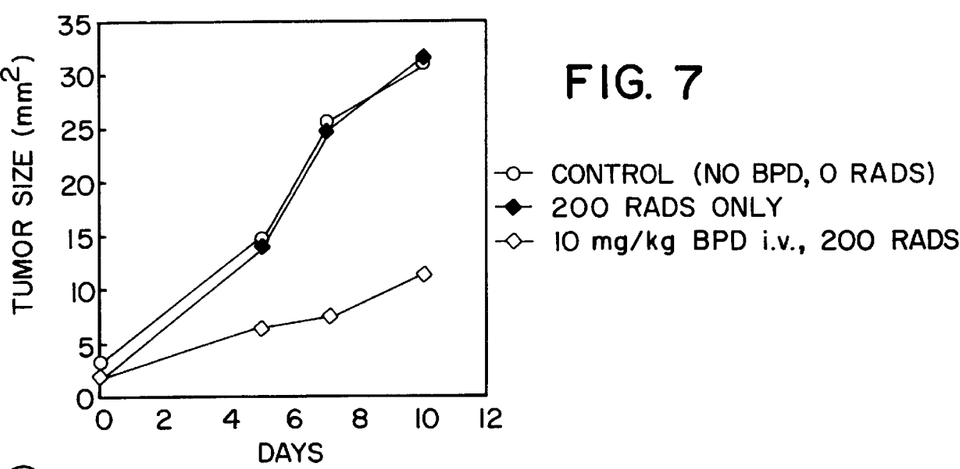
FIG. 7 shows the effect of initial radiation and subsequent BPD-MA treatment on the in vivo growth of P815 tumors in DBA/2 mice.

As is shown in FIG. 7, irradiation with 200 rads of gamma-radiation resulted in nearly the same tumor growth as did the no drug/no radiation treatment. The test in which the introduction of the drug was followed by 200 rads of $^{60}$Co irradiation showed significantly lower tumor size at all times up to 10 days, the time at which the test was stopped.

Example 6

This example also shows the effects of BPD-MA and subsequent radiation treatment on the in vivo growth of P815 cells in DBA/2 mice.

In this example, DBA/2 mice were intravenously injected with 5×10⁴ P815 cells. Two days later, the mice were injected with liposomal BPD-MA at 10 mg/kg and, one hour later, exposed to whole body irradiation from a $^{60}$Co source at a level of 200 rads per mouse. Two control groups were also formed: mice injected with P815 cells and given no further treatment and mice injected with P815 cells and exposed to 200 rads of $^{60}$Co radiation. On each of days four and seven after the irradiation, three mice from each group were sacrificed and the number of P815 cells in their spleens was determined using the limiting dilution method. The evaluation and counting of P815 cell colonies in culture was then carried out. The total load of P815 cells in each group was determined.

Figure 8:
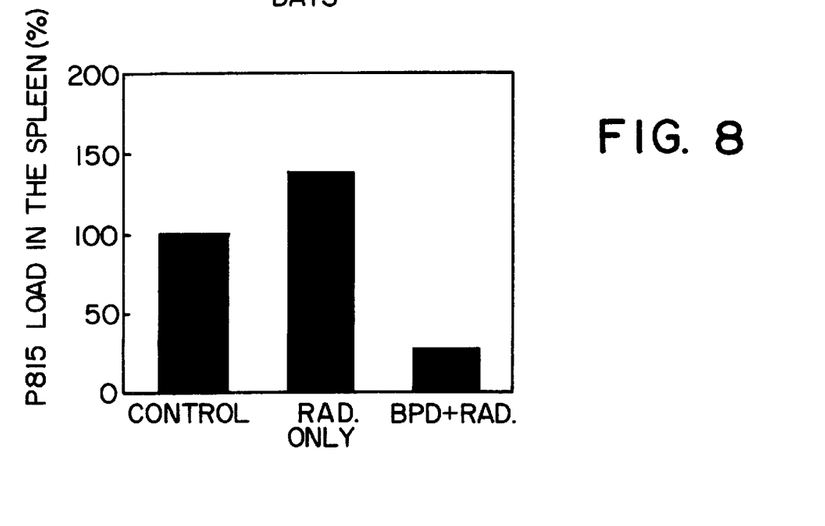
FIG. 8 shows the effect of initial BPD-MA and subsequent irradiation upon the presence of P815 cells in DBA/2 mice spleens.

FIG. 8 shows the total load of P815 cells in the spleens of the mice from the various groups on day seven. Clearly, the load for the treatment according to the process of the invention is superior to those of the two control groups.

The invention has been described by a direct description and by examples. As noted above, the examples are meant to be only examples and not to limit the invention in any meaningful way. Additionally, one having ordinary skill in this art in reviewing the specification and claims which follow would appreciate that there are equivalents to those claimed aspects of the invention. The inventors intend to encompass those equivalents within the reasonable scope of the claimed invention.

We claim as our invention:

1. An in vitro process for (i) the destruction of, or (ii) inhibiting the growth of or the recovery from gamma radiation of tumor cells which are sensitive to BPD-MA, which process comprises:

a. radio-sensitizing said tumor cells by providing to said cells in vivo a radio-sensitizing amount of a compound of the formula wherein:
R¹ and R² are —COO-alkyl where alkyl is a hydrocarbon of 1–6 carbon atoms,
one R is H, and
the other R is alkyl (1–6C); and b. subjecting said tumor cells in vitro to ionizing gamma radiation of less than 500 rad.

2. The process of claim 1 wherein $R^1$ and $R^2$ are independently carbomethoxy or carboethoxy and wherein R is methyl or ethyl.

3. The process of claim 1 wherein said ionizing gamma radiation is 10–200 rad.

4. The process of claim 1 wherein said compound is provided as a pharmaceutical composition.

5. The process of claim 4 wherein said composition comprises liposomes as a pharmaceutically acceptable excipient.

6. An in vitro or in vivo process for (i) the destruction of or (ii) inhibiting the growth of or the recovery from gamma radiation of tumor cells which are sensitive to BPD-MA in a body fluid, wherein said process comprises:

a. providing said cells in said body fluid with a radio-sensitizing amount of a compound of the formula wherein:
$R^1$ and $R^2$ are —COO-alkyl where alkyl is a hydrocarbon having 1–6 carbon atoms,
one R is H, and
the other R is alkyl (1–6C); and b. subjecting said cells in said body fluid to ionizing gamma radiation of less than 500 rad.

7. The process of claim 6 wherein $R^1$ and $R^2$ are independently carbomethoxy or carboethoxy and wherein R is methyl or ethyl.

8. The process of claim 6 wherein said ionizing gamma radiation is 10–200 rad.

9. The process of claim 6 wherein said compound is provided as a pharmaceutical composition.

10. The process of claim 9 wherein said composition comprises liposomes as a pharmaceutically acceptable excipient.

11. The process of claim 6 which is conducted in vivo and wherein said compound is provided to said cells by administering said compound to a subject containing said fluid.

12. The process of claim 6 wherein said radio-sensitizing amount of said compound is provided to said cells by a process which comprises removing said fluid from a subject and contacting said fluid with said compound in vitro.

13. The process of claim 6 wherein said step of subjecting said cells to ionizing gamma radiation is preceded by the step of removing said fluid from a subject.

14. A process for (i) the destruction of or (ii) inhibiting the growth of or the recovery from gamma radiation of tumor cells in a subject which cells are sensitive to BPD-MA after subjecting said cells to ionizing gamma radiation, said process comprising the steps of:

a. radio-sensitizing said tumor cells in said subject by providing to said cells a radio-sensitizing amount of a compound of the formula wherein:
$R^1$ and $R^2$ are —COO-alkyl where alkyl is a hydrocarbon having 1–6 carbon atoms,
one R is H, and
the other R is alkyl (1–6C); and b. subjecting said cells in said subject to ionizing gamma radiation of less than 500 rad.

15. The process of claim 14 wherein $R^1$ and $R^2$ are independently carbomethoxy or carboethoxy and wherein R is methyl or ethyl.

16. The process of claim 14 wherein said ionizing gamma radiation is 10–200 rad.

17. The process of claim 14 wherein said BPD-MA is provided as a pharmaceutical composition.

18. The process of claim 17 wherein said composition comprises liposomes as a pharmaceutically acceptable excipient.

19. The process of claim 14 wherein said subject is a human.

* * * * *